United States Patent
Arkles et al.

(10) Patent No.: US 10,933,008 B1
(45) Date of Patent: Mar. 2, 2021

(54) SILICON-BASED CANNABIDIOL DERIVATIVES AND COMPOSITIONS THEREOF

(71) Applicant: Gelest Technologies, Inc., Morrisville, PA (US)

(72) Inventors: Barry C. Arkles, Pipersville, PA (US); Jonathan D. Goff, Philadelphia, PA (US); Taewoo Min, Langhorne, PA (US); Youlin Pan, Langhorne, PA (US); Tatyana Abel-Roberman, Bryn Athyn, PA (US)

(73) Assignee: GELEST TECHNOLOGIES, INC., Morrisville, PA (US)

( * ) Notice: Subject to any disclaimer, the term of this patent is extended or adjusted under 35 U.S.C. 154(b) by 0 days.

(21) Appl. No.: 16/879,999

(22) Filed: May 21, 2020

Related U.S. Application Data

(60) Provisional application No. 62/925,945, filed on Oct. 25, 2015.

(51) Int. Cl.
*A61K 8/58* (2006.01)
*C07F 7/08* (2006.01)
*C07F 7/18* (2006.01)

(52) U.S. Cl.
CPC ............ *A61K 8/585* (2013.01); *C07F 7/0838* (2013.01); *C07F 7/0874* (2013.01); *C07F 7/1804* (2013.01)

(58) Field of Classification Search
None
See application file for complete search history.

(56) References Cited

FOREIGN PATENT DOCUMENTS

| WO | 2009018389 A1 | 2/2009 |
| WO | 2018096504 A1 | 5/2018 |
| WO | 2018148787 A1 | 8/2018 |

OTHER PUBLICATIONS

Boggs et al., "Clinical and Preclinical Evidence for Function Interactions of Cannabidiol and D9-Tetrahydrocannabinol," Neuropsychopharmacology Reviews, vol. 43, pp. 142-154 (2018).
Karsak et al., "Attenuation of Allergic Contact Dermatitis Through the Endocannabinoid System," Science, vol. 316, pp. 1494-1497 (2007).
International Search Report and Written Opinion dated Jul. 15, 2020 in International Application No. PCT/US2020/033918.

*Primary Examiner* — Joseph R Kosack
(74) *Attorney, Agent, or Firm* — Panitch Schwarze Belisario & Nadel LLP

(57) ABSTRACT

Silicon-based cannabidiol derivatives and methods for their synthesis are provided, in which the derivatives contain a cannabidiol molecule and at least one silicon-based group containing Si—O—Si bonds. The derivatives are useful in cosmetic and topical compositions, have potential beneficial topical properties, and enhance solubility and compatibility in cosmetic formulations containing the silicon-based materials. Silicone elastomers infused with compositions containing the silicon-based cannabidiol derivatives and trisiloxanes are also provided.

25 Claims, No Drawings

SILICON-BASED CANNABIDIOL DERIVATIVES AND COMPOSITIONS THEREOF

CROSS-REFERENCE TO RELATED APPLICATION

This application claims priority to U.S. Provisional Application No. 62/925,945, filed Oct. 25, 2019, the disclosure of which is herein incorporated by reference.

BACKGROUND OF THE INVENTION

Cannabidiol is a phytocannabinoid which is believed to have anti-inflammatory activity. It is one member of a family of structurally related compounds that exhibit biological action while exhibiting little or no neuropsychopharmacologic effects (D. L. Boggs *Neuropsychopharmacology;* 43(1): 142-154; 2018). Cannabidiol is the designated name for 2-[(1R,6R)-3-methyl-6-(1-methylethenyl)-2-cyclohexen-1-yl]-5-pentyl-1,3-benzenediol, shown below:

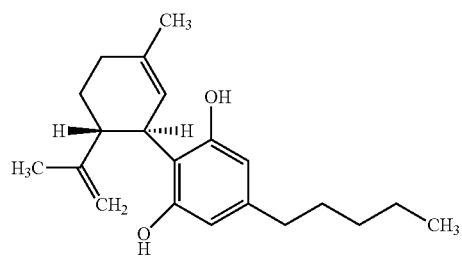

(I)

Topical formulations of cannabidiol have been reported to have apparent therapeutic benefits in reducing pruritus and other localized pain and discomfort (Karsak et al, *Science,* 316, 1494-1497; (2007)). Pure cannabidiol is a solid with poor spreadability and limited solubility in vehicles commonly used in topical and personal care applications. Therefore, cannabinoid derivatives with improved solubility would be desirable.

BRIEF SUMMARY OF THE INVENTION

A silicon-based cannabidiol derivative according to an embodiment of the disclosure comprises at least one silicon-based functional group containing Si—O—Si bonds which is bound to a cannabidiol molecule having Formula (I):

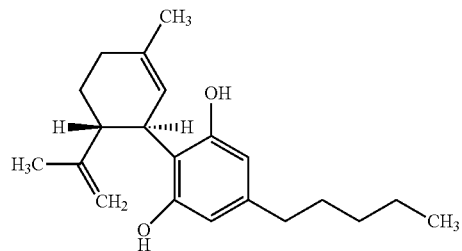

(I)

A cosmetic or topical composition according to an embodiment of the disclosure comprises a base formulation and at least one silicon-based cannabidiol derivative comprising at least one silicon-based functional group containing Si—O—Si bonds which is bound to a cannabidiol molecule having Formula (I):

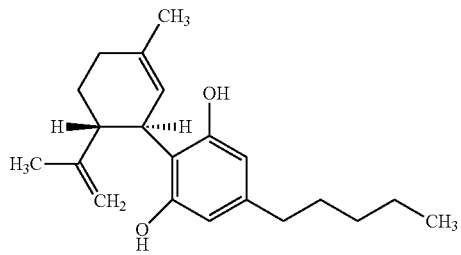

(I)

DETAILED DESCRIPTION OF THE INVENTION

The disclosure relates to compositions containing silicone-soluble derivatives of cannabidiol (CBD) that are useful for various applications, including formulation into topical medicinal products and personal care products, and methods for their preparation. The silicon-based derivatives of cannabidiol described herein are unique hybrid organosilicon compounds formed by attaching cannabidiol to a siloxane backbone, also described as a molecule comprising at least one silicon-based functional group containing Si—O—Si bonds which is bound to a cannabidiol molecule. The cannabidiol substituent adds skin treatment properties to the siloxane backbone, while the siloxane component improves the emolliency slip and skin feel of the cannabidiol. This unique structure enables the organosilicon-modified cannabinoid compounds to behave as solubilizing agents in a number of cosmetic vehicles, including mineral and vegetable waxes, as well as underivatized cannabinoids. This is of significance because the lack of solubility and poor spreadability of topical formulations of underivatized cannabinoid compounds is an obstacle to applying uniform thin films of desired composition and activity. While the compositional products described herein may or may not exhibit transepidermal activity, their ability to act as vehicles for uniform distribution of cannabinoids has the potential to enhance the pharmacologic activity of the unmodified cannabinoids associated with the endocannabinoid receptors by allowing lower level and more uniform transdermal activity.

Preferred embodiments of the compounds of the disclosure include trisiloxanyl derivatives of cannabidiol in which a silane-based group is bound through one or both of the phenolic hydroxyl groups of the cannabidiol molecule (in the benzenediol ring), derivatives in which silicon group(s) is/are attached to the benzenoid ring of the cannabidiol molecule by replacement of the hydrogens of the hydroxyl group(s), and derivatives in which a silicon-based group is bound to the terpenyl (isopropenyl) group of the cannabidiol (such as by hydrosilylation of the unsaturated bond and formation of a silicon-carbon bond). It is also within the scope of the disclosure for the cannabidiol derivative to contain three silicon-containing groups, such as one group at the terpenyl group of the cannabidiol and two groups bound through the two phenolic hydroxyl groups, provided that such a derivative has sufficient solubility.

As used herein, the term "cannabidiol" is intended to encompass all cannabidiol isomers, as those compounds are found naturally or synthetically, as well as derivatives thereof such as cannabidiol acid (including derivatives prepared for use in cosmetic and topical formulations) unless otherwise particularly specified.

The silicon-based cannabidiol derivatives include a cannabidiol molecule, such as shown in Formula (I), which as noted above may be any of the naturally occurring or synthesized cannabidiols as defined herein, having at least one silicon-based group as a functional group. Most preferably, the silicon-based group is a siloxanyl group or a trialkoxysilane-containing group.

Preferred cannabidiol derivatives, described herein, have a structure in accordance with Formula (I) above in which the phenolic hydroxyl group(s) or terpenoid carbon groups are bound to a siloxane moiety containing two or more silicon atoms, preferably three or more, silicon atoms, most preferably about 3 to about 10 silicon atoms.

Cannabidiol derivatives according to embodiments of the disclosure have general formulas (A), (B), and (C), (D), (E), and (F): the compounds having formulas (A), (B), and (C) contain one silicon-based functional group; the compounds having formulas (D) and (E) contain two silicon-based functional groups, and the compound having formula (F) contains three silicon-based functional groups. In these formulas, in which "Me" is $CH_3$, $R^1$, $R^2$, and $R^3$ may each be independently, for example and without limitation, $SiMe(OSiMe_3)_2$ or $SiMe_2(OSiMe_2)_4CH_2CH_2CH_2CH_3$. However, compounds having formulas (A) to (F) that are within the scope of the disclosure are not limited to these substituents, and other silicon-containing functional groups having Si—O—Si bonds that are known in the art or to be developed would also be suitable for $R^1$, $R^2$, and $R^3$.

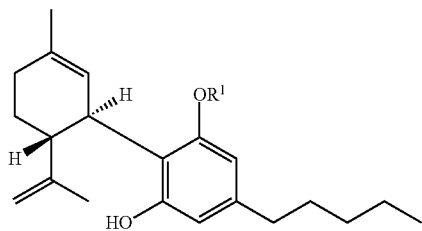
(A)

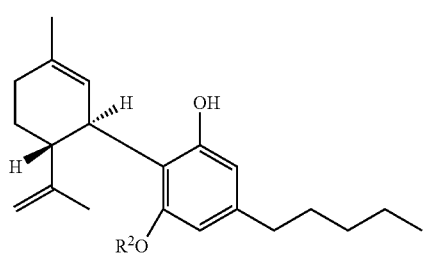
(B)

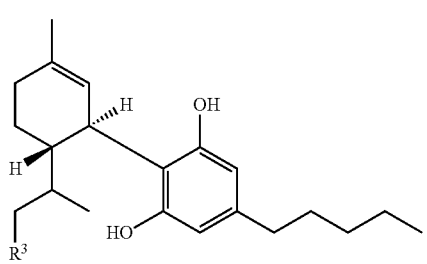
(C)

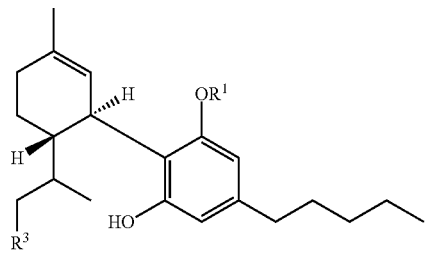
(D)

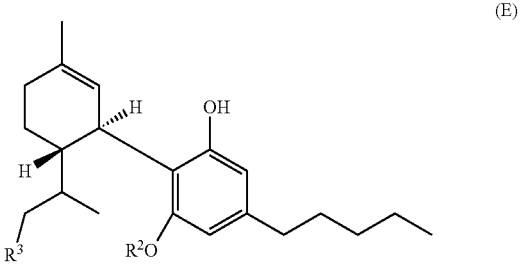
(E)

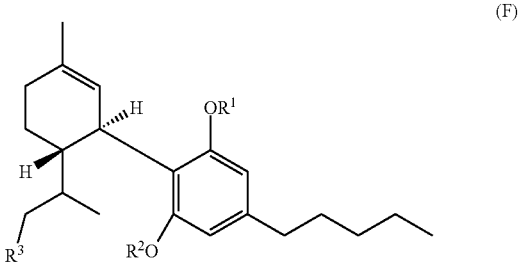
(F)

The silicon-based cannabidiol derivatives according to embodiments of the disclosure thus include a wide variety of derivatized compounds, including most preferred compounds such as, for example, (cannabidioloxypropyl)heptamethyltrisiloxane (formula (II)), (cannabidioloxy)heptamethyltrisiloxane (formula (III)), cannabidioloxypropyltriethoxysilane, and cannabidioloxypropyl-terminated polydimethylsiloxane (formula (IV)), three of which are shown below:

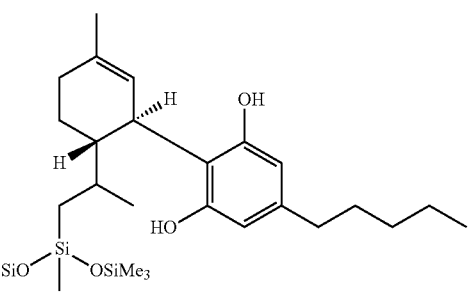
(II)

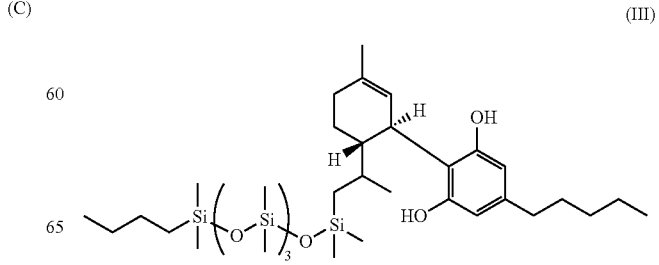
(III)

(IV)

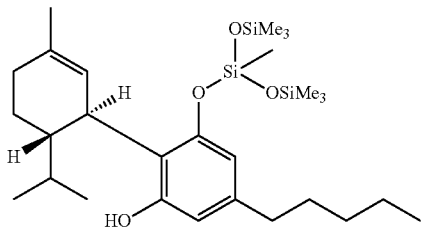

An exemplary compound having two silicon groups on the cannabidiol (general formula (E)) has specific formula (V):

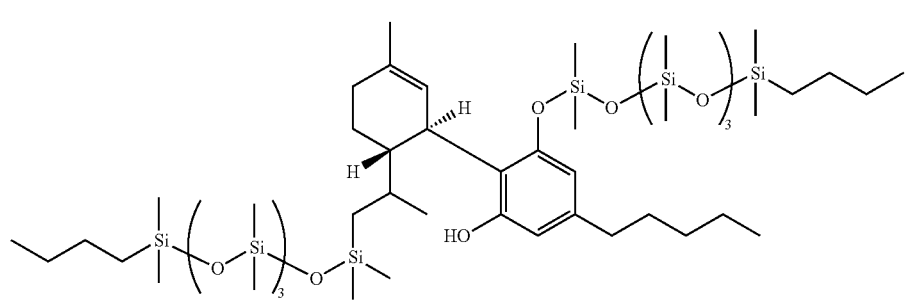

Compounds according to embodiments of the disclosure may thus contain a direct ether linkage between the silicon-containing functional group and the phenolic hydroxyl groups of the cannabidiol molecule (direct Si—O bond), or may contain a hydrocarbon bridge between the isopropenyl group of cannabidiol and the silicon molecule in the silicon-based group (direct Si—C bond).

The compounds described herein have a broad range of solubility in and compatibility with materials typically used in the formulation of skin care and color cosmetics. They also have the additional advantage of being more resistant to becoming rancid or colored during formulation. Specifically, the substitution at the phenolic oxygen(s) of the cannabidiol in one embodiment reduces the tendency of the compounds to become rancid. This may be due to inability of the substituted oxygen to intercept radical species and/or due to an increase in the oxygen permeability of the material.

With respect to certain of the derivatives including a direct —Si—O— bond (i.e., the unbridged derivatives), the phenolic oxygen(s) is/are directly bound to silicon, which allows the cannabidiol derivatives of this embodiment to slowly hydrolyze and release free cannabidiol, potentially resulting in reducing dermal inflammation. Advantageously, the silylated (bridged) derivatives (i.e., those having a silylated alkyl (—Si—C—) bond on the cannabidiol ring) are hydrolytically stable.

Additionally, certain of the derivatives (for example, the siloxanylcannabidiols) when spread in a thin film on the skin, slowly hydrolyze, liberating cannabidiol for which anti-inflammatory activity has been reported. The phenolic siloxy compounds are not hydrolytically stable. Exposure of these compounds to moisture will result in slow decomposition, forming cannabidiol and low molecular weight siloxanes. Thus, the compounds are storage stable but in use can potentially demonstrate bioactivity.

Unlike many silicones and silicone derivatives, these compounds are easily incorporated into cosmetic products such as skin-care and color cosmetics, including lipsticks and foundations, due to their solubility in a range of polar compounds such as castor oil and a variety of cosmetic esters. They may also act as co-solvents for cannabidiols and silicones. Further, due to such solubility, these derivatives may be useful as compatibilizers for bioactives, cannabidiols, and silicone, among other possible applications.

The cannabidiol derivatives described herein may be prepared in various ways. In accordance with one embodiment of the disclosure, the compounds may be prepared by forming a direct ether linkage between the derivatized group and a phenolic hydroxyl group of cannabidiol or by forming a hydrocarbon bridge between the isopropenyl (terpenyl) group of cannabidiol and the silicon molecule in the silicon-based group. The derivatives described herein in which the silicon-based functional group is bonded with an Si—O bridge to the cannabidiol may also be prepared by hydrosilylation of the isopropenyl group or by reacting a hydroxyl group of the benzenediol ring of the cannabidiol with an allylic halide in a solvent to form an allyloxycannabidiol intermediate having a direct ether linkage at the position of the hydroxyl group, and then reacting the intermediate with a silane compound and a catalyst to form a silicon-based cannabidiol derivative.

It is also within the scope of the disclosure to form a silylated ether (—Si—O—C) on the cannabidiol or to form a silylated ether without a hydrocarbon bridge (—Si—O—) on the cannabidiol. The —Si—O—C bond maybe formed by reaction of the C—OH group via a silylation reaction, such as the reaction of a chlorine-containing siloxane compound (—Si—Cl) with a hydroxyl group HO—C in the presence of a base acceptor, or the dehydrogenative coupling of a hydride-containing siloxane (—Si—H) with a hydroxyl group. Another possible method of forming the Si—O—C bond is by forming an intermediate alkali metal alkoxide such as C—O—Na and reacting it with either a Si—Cl or Si—H containing compound. Reaction to form a hydrocarbon bridge proceeds by the addition of a hydride containing siloxane (—Si—H) across a C=C double bond by a hydrosilylation reaction.

The silane compounds used in the reactions described above may be any of a wide variety of silicon-based compounds, and preferably include alkylsilanes, alkoxysilanes, alkylsiloxanes and alkoxysiloxanes and their derivatized or functionalized counterparts. In general, it is preferred to have two or more silicon atoms in the substitution in order to provide solubility and spreading characteristics suitable for topical creams and ointments. Examples include, without limitation, bis(trimethylsiloxy)methylsilane, bis(trimethylsiloxy)ethylsilane, bis(trimethylsiloxy)propylsilane, bis(triethylsiloxy)methylsilane, bis(triethylsiloxy)ethylsilane, bis(triethylsiloxy)propylsilane, triethoxysilane, trimethoxysilane, tripropylsilane, bis(tripropylsiloxy)methylsilane, bis(tripropylsiloxy)ethylsilane, bis(tripropylsiloxy) propylsilane and similar compounds.

Also useful as silane compounds herein are polymeric silicon-containing molecules having similar reactive capabilities as the silane monomeric structures noted above, such as polydimethylsiloxane, polydiethylsiloxane, polydipropylsiloxane, polymethylethylsilane, polymethylpropylsiloxane, and other polyalkyl- or polyalkenyl-siloxanes as are known in the art or to be developed. Chain lengths may vary, but it is preferred that the molecular weight (Mn) of polymeric silane compounds used to form polymeric silicon-based derivative groups on cannabidiol be from 100 to about 5000, and most preferably from about 500 to about 2000. It should be noted that variations in molecular weight above and below this range are within the scope of the disclosure and that the components having different chain lengths may contribute varying properties accordingly. For example, generally, lower molecular weight chains would tend to be more emollient in nature, while higher molecular weight chains would tend to be more substantive in terms of being longer-wearing on skin and more resistant to wash-off.

It should also be understood that the derivatives described herein may be produced using pure cannabidiol. Alternatively, the derivatives may be formed and provided as a component of phytocannabinoid and/or other phytochemical mixtures. For example, the cannabidiol derivative of hemp oil and hemp oil extracts may be formed without isolating the pure cannabidiol component. The cannabidiol derivative according to the disclosure may comprise less than about 1% of the product, such as hemp oil or hemp oil extract. Further, compositions according to the disclosure may contain one or more of the derivatives described herein and one or more phytochemicals extracted from hemp oil.

The silicon-based cannabidiols described herein may be used in various cosmetic and topical compositions, including preferably those which have silicon compounds or silicone based polymers in the base formulation because the derivatives facilitate compatibility and solubility in such compounds within formulations. However, the disclosure is not limited to those cosmetic compositions and may include any cosmetic composition in which the silicon-based cannabidiol derivatives are useful. The cosmetic and topical compositions of the present disclosure include a cosmetic base formulation, which may be any suitable cosmetic or topical base formulation as described above and at least one silicon-based cannabidiol derivative as described herein. The silicon-based cannabidiol derivatives include a cannabidiol molecule or a commercial or natural derivative thereof and include a silicon-based group bonded to the cannabidiol molecule (or the derivative thereof) by way of the benzenediol group, more particularly through the oxygen atom of the ring, or through the isopropenyl (terpenyl) group, as described above.

Typical cosmetic base formulations for use with the silicon-based cannabidiol derivatives described herein include, without limitation creams, lotions, sunscreens, lipsticks, cream eyeshadows, blush, antiaging creams, sunburn creams, self-tanning lotions, foundation and hair cosmetics.

When incorporated in such formulations, it is preferred that the silicon-based cannabidiol derivative is present in an amount of about 0.01 percent by weight to about 20 percent by weight, preferably about 0.5 percent by weight to about 5 weight percent and most preferably about 0.5 to about 1.0 percent by weight based on the weight of the formulation.

If a silicon compound or silicone polymer is additionally included in the formulation, it may include compounds or polymers such as organopolysiloxane polymers or cross-linked elastomers as are known in the art or to be developed. However, other polymer base materials may also be used in the base formulation, whether natural or synthetic, including sodium alginate, carrageen, agar, guar gum, methyl cellulose, ethyl cellulose, hydroxypropyl cellulose, carboxymethyl cellulose, starch and starch derivatives, albumin, casein, gelatin, polyacrylates and salts thereof, polyacrylic amides, carboxyvinyl polymers, polyethylene imines, polyethylene glycol, polyols, polyether polyols, polyvinyl alcohols, polyvinyl pyrrolidones, polyvinyl ethers, polyacrylic acids, polymethacrylic acids, maleic acid polymers, polyamides, and the like.

Other components for use in the cosmetic base formulation include, but are not limited to, metal oxides, polyolefins, sunscreen active agents such as UVA and/or UVB absorbing materials (organic and inorganic); oils such as silicone oils, oil emulsions (water-in-oil, water-in-silicone, combinations thereof); natural fats, fatty acids, fatty oils and alcohols (avocado oil, almond oil, olive oil, sesame seed oil, rice oil, corn oil, safflower oil, soybean oil, rape seed oil, palm oil, castor oil, high oleic sunflower oil, coconut oil, tallow oil, meadowfoam and similar compounds, lauric acid, myristic acid, stearic acid, isostearic acid, triisostearic acid, behenic acid, oleic acid, isostearyl citrate, triisostearyl citrate, glyceryl stearate, sorbitan stearate, ocyldocecyl stearate, linoleic acid, cetyl alcohol, isostearyl alcohol, ceteareth, ceteareth alcohol, decanol, octyldodecanol); waxes (jojoba oil, canauba wax, candelilla wax, rice bran wax, lanolin, beeswax, montan wax, microcrystalline wax, ceresin and similar waxes), emulsifiers and base formulators (including surfactants and emulsifiers of the non-ionic, anionic, cationic, zwitterionic and amphoteric, parabens, methylparabens, propylparabens, and polymeric materials such as polyoxyalkylene polymers and copolymers, polyethers, polyether polyols, polyglycols, polyalkylene glycols, polyglycerins, polydimethicones and similar polymers and mixtures, combinations and copolymers thereof); saccharides (mannitol, xylitol, sorbitol, pentaerythritol, erythritol, glucose, sucrose, fructose, lactose and the like) and additives such as microspheres, humectants, exfoliants, emollients, gelling agents, amino acids, enzymes and peptides, proteins, polysorbates, alkylamines, other vitamin and vitamin derivatives, including other cannabidiols, tocotrienols and derivatives thereof, anti-acne components, flavonoids, EDTA and salts thereof, skin soothing agents, fragrances, colorants (pigments and dyes in various color combinations whether natural or synthetic, metallic oxides), herbal components and extracts, natural or synthetic oils, mica, talc and other similar fillers, antioxidants, chelators, antifungals, antibacterial agents, antimicrobial agents, antiseptics and medicaments. The amounts and ratios of these components may vary in accordance with the nature of the formulation or intended use of the cosmetic formulation and the components and amounts thereof are not intended to be limited herein.

Aspects of the disclosure also relate to compositions containing the silicon-based cannabidiols described herein and an N-alkylheptamethyltrisiloxane, such as, without limitation, methylheptamethyltrisiloxane, ethylheptamethyltrisiloxane, n-propylheptamethyltrisiloxane, butylheptamethyltrisiloxane, etc. It is also within the scope of the disclosure to include an alternative siloxane material in which the silicon cannabidiol is soluble. The presently preferred siloxane is n-propylheptamethyltrisiloxane. It has been found that these compositions spread to a thin film which, when exposed to moisture (such from the skin or the air), release and reform CBD.

Such "slow release cannabidiol compositions" may be infused into various silicone substrates, such as silicone elastomers, silicone fluids, other silicone gel matrices, and other silicone-based formulations. When these infused materials are applied to the skin, moisture from the skin or the air releases the CBD, providing effective soft skin adhesives, scar reduction treatments, transdermal patches, anti-wrinkle face masks and patches, and other similar applications. The release of CBD from a silicone gel elastomer infused with silylated-CBD upon hydrolysis is shown in the following schematic.

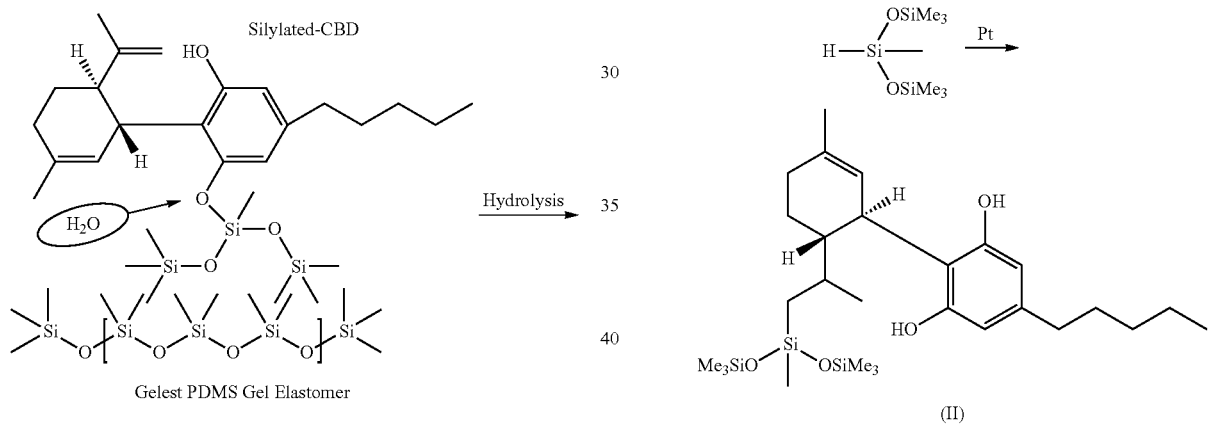

The invention will now be described in connection with the following, non-limiting examples.

Example 1: Synthesis of 2-[(R,6R)-3-Methyl-6-(1-methyl-2-(bis(trimethylsiloxy)methylsilyl)ethyl)-2-cyclohexen-1-yl]-5-pentyl-1,3-benzenediol

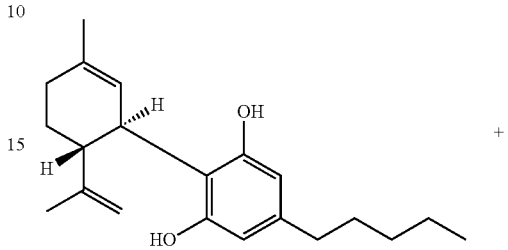

(II)

Bis(trimethylsiloxy)methylsilane (21.36 g, 0.10 mol) and Karstedt catalyst (2% Pt concentration in xylene, 1 mL) were charged to a reactor. A solution of cannabidiol (25.16 g, 0.08 mol) in toluene (21.89 g) was added dropwise over 30 min while keeping pot temperature below 30° C. The resulting reaction mixture was stirred at room temperature for 2 h, then filtered through silica gel (80 g) and washed with toluene (800 g). The filtrate was concentrated in vacuo. The residue was the product (32.0 g, 74%) as orange oil. Analytical data: R.I. 1.488 @ 25° C.; $^1$H NMR (400 MHz, CDCl$_3$) δ 6.23 (bs, 2H), 6.00 (bs, 1H), 5.52 (s, 1H), 4.63 (bs, 1H), 3.81 (dd, J=6.0, 2.4 Hz, 1H), 2.47-2.41 (m, 2H), 2.23-2.05 (m, 1H), 1.76-1.73 (m, 3H), 1.62-1.55 (m, 6H), 1.38-1.25 (m, 6H), 0.90-0.82 (m, 6H), 0.146 (dd, J=14.0, 12.4 Hz, 1H), 0.08 (s, 9H), 0.07 (s, 9H), 0.00 (s, 3H); FTIR (cm$^{-1}$): 3435, 2956, 2929, 2873, 2858, 1628, 1582, 1514, 1443, 1377, 1251, 1218, 1039, 1025; GC-MS m/z: 536 (M), 521 (M-Me), 446 (M-OSiMe$_3$).

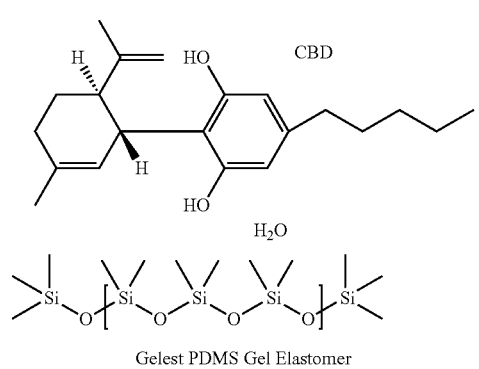

Example 2: Synthesis of 2-[(1R,6R)-3-Methyl-6-(1-methyl-2-(1-butyl-1,1,3,3,5,5,7,7-octamethyltetrasiloxy-dimethylsilyl)ethyl)-2-cyclohexen-1-yl]-5-pentyl-1,3-benzenediol (III)

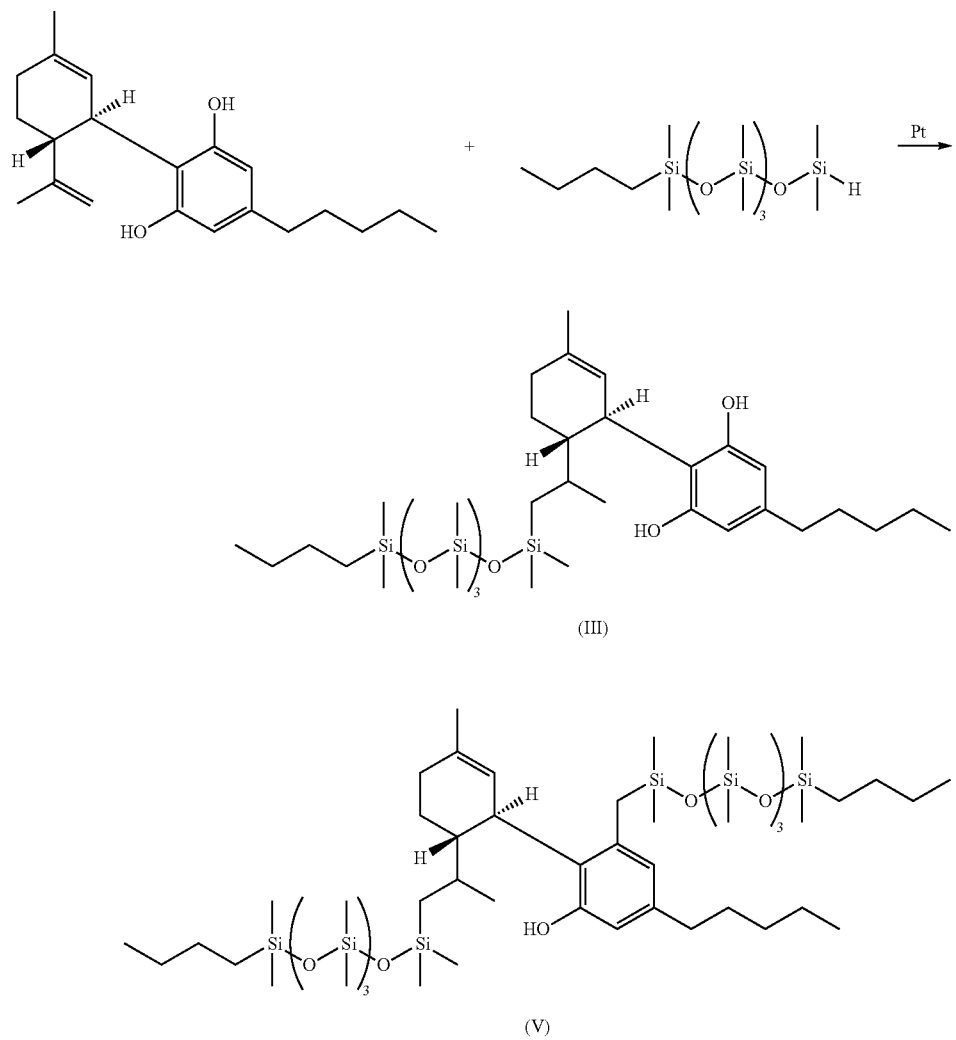

(III)

(V)

1-Butyl-1,1,3,3,5,5,7,7,9,9-decamethylpentasiloxane (34.89 g, 0.08 mol) and Karstedt catalyst (2% Pt concentration in xylene, 1 mL) were charged to a reactor. A solution of cannabidiol (20.44 g, 0.07 mol) in toluene (17.78 g) was added dropwise over 30 min while keeping pot temperature below 50° C. The resulting reaction mixture was heated at 40° C. for 3-5 h, filtered through silica gel (50 g) and washed with toluene (400 g). The filtrate was concentrated in vacuo. The residue contained the desired product (III) and a by-product (V) (ratio 9:1, 46.7 g) as viscous orange liquid. Analytical data: R.I. 1.462 @ 25° C.; d: 1.019 g/mL; $^1$H NMR (400 MHz, CDCl$_3$) δ 6.26 (bs, 1H), 6.15 (bs, 1H), 6.01 (bs, 1H), 5.52 (s, 1H), 5.12 (bs, 1H), 3.84-3.81 (m, 1H), 2.46-2.41 (m, 2H), 2.15-2.06 (m, 1H), 1.76-1.55 (m, 9H), 1.35-1.25 (m, 12H), 0.9-0.87 (m, 12H), 0.56-0.52 (m, 3H), 0.12-0.03 (m, 32H); FTIR (cm$^{-1}$): 3451, 2958, 2926, 1628, 1583, 1444, 1257, 1219, 1022.

Example 3: Synthesis of 2-[(1R,6R)-3-Methyl-6-(1-methylethenyl)-2-cyclohexen-1-yl]-5-pentyl-1-(bis(trimethylsiloxy)methylsiloxy)-3-ol-benzene (IV)

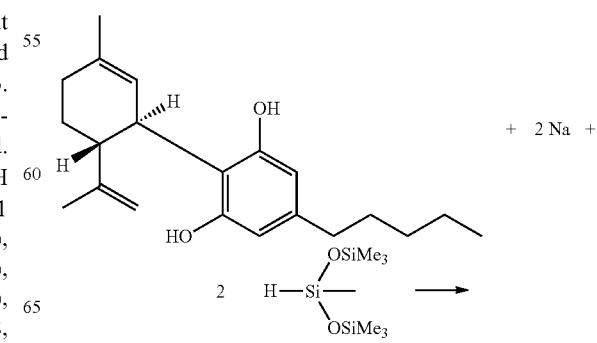

-continued

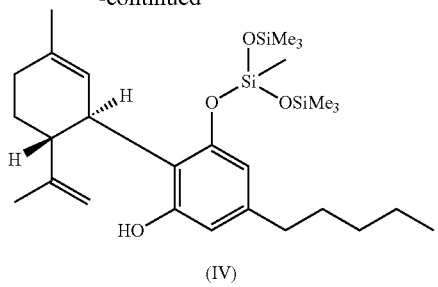

(IV)

Sodium (0.77 g, 0.03 mol) and tetrahydrofuran (13.42 g) were charged to a reactor. A solution of cannabidiol (5.03 g, 0.02 mol) in tetrahydrofuran (37.98 g) was added dropwise over 30 min while keeping pot temperature below 70° C. The resulting reaction mixture was stirred at room temperature until all sodium was consumed. Bis(trimethylsiloxy)methylsilane (14.24 g, 0.06 mol) was added dropwise over 10 min at 70° C., then the reaction mixture was heated at 110-120° C. for 10 h. The reaction mixture was filtered through silica gel (40 g) and washed with tetrahydrofuran (400 g). The filtrate was concentrated in vacuo, then the residue was purified by flash-over distillation. The distillate contained the produce and unreacted cannabidiol (9:1 mixture, 8.4 g) as a clear viscous liquid. Analytical data: R.I. 1.453 @ 25° C.; d=1.001 g/mL; FTIR (cm$^1$): 3458, 2958, 2927, 2857, 1622, 1574, 1436, 1376, 1251, 1037.

Example 4: Solubility Studies

Cannabidiol isolate (CBD) having formula (I) and three silylated CBD derivatives as described in Examples 1, 2, and 3 above were evaluated for solubility in a number of the most common oils and silicones at room temperature and the data are summarized in Table 1 below ("S"=soluble, "I"=insoluble). It may be concluded that the CBD isolate was soluble in all oils and insoluble in all silicones and water. The CBD derivatives were insoluble in water and soluble in both oils and silicones (heating was required for the derivative of Example 1). The derivative of Example 2 was only partially soluble in castor oil (even with partial heating). Thus, the presence of the silicon-containing groups increased the solubility of CBD in all silicones tested.

TABLE 1

Solubility Study Results

| Vehicle | CBD | Example 1 CBD Silylated | Example 2 CBD Silylated | Example 3 CBD Silylated |
|---|---|---|---|---|
| Almond oil | S | S (with heating) | S | S |
| Castor Oil | S | S (with heating) | Partial (with heating) | S |
| Isopropyl Mitystate | S | S (with heating) | S | S |
| Ethylhexyl Palmitate | S | S (with heating) | S | S |
| Octododecanol | S | S (with heating) | S | S |
| Triglycerides | S | S (with heating) | S | S |
| Sunflower Oil | S | S (with heating) | S | S |
| Mineral Oil | S | S (with heating) | S | S |
| Water | I | I | I | I |
| SiBrid ™ 031 | I | S (with heating) | S | S |
| SiBrid ™ 081 | I | S (with heating) | S | S |
| Diethieone 12 | I | S (with heating) | S | S |
| Dimethicone | I | S (with heating) | S | S |
| Cyclomethicone | I | S (with heating) | S | S |

Example 5: Preparation and Analysis of Slow Release Cannabidiol Compositions A solution was prepared by adding 5 g of the trisiloxanyl-cannabidiol product (IV) prepared in Example 3 and 5 g of n-propylheptamethyltrisiloxane (commercially available from Gelest) to a 20 ml vial. Sample 1 was prepared by inserting apiece of silicone elastomer (1.5 cm×2.5 cm, 0.35 g, commercially available from Gelest) into a 20 ml vial containing the solution and letting the vial sit with a closed lid for 30 minutes to absorb the solution into the elastomer. Sample 2 (control) was an identical piece of silicone elastomer which was inserted into a 20 ml vial containing hemp seed oil and let sit with a closed lid for 30 minutes to absorb the hemp oil into the elastomer.

After 30 minutes, Samples 1 and 2 were removed from the vials, excess solution was removed using tissue paper, and the resulting silicone pieces were weighed and visually inspected. Sample 1 had changed color from opaque to clear with a yellow tint, increased weight by 400% (now weighting 1.41 g), and swelled to 2×3 cm. Sample 2 did not change color, weight, or size.

Sample 1 was washed in water three consecutive times. For each wash, the sample was placed in a vial containing 10 g of DI water and shaken for 10 seconds. The water from each wash was collected and analyzed for the presence of CBD using a basic thin-layer chromatography (TLC) method using 20% ethyl acetate in hexanes. CBD isolate was compared to a hydrolyzed sample of trisiloxanyl-cannabidiol product (IV) as well as all three washes. The plate showed one dark brown spot in the CBD isolate column. All other samples showed, in addition to four other spots, brown spot as the CBD isolate starting material, indicating the formation of underivatized CBD. This proved that all washes contained CBD, evidence that the silylated cannabidiol underwent hydrolysis to release CBD, as shown in the schematic above.

It will be appreciated by those skilled in the art that changes could be made to the embodiment described above without departing from the broad inventive concepts thereof. Also, based on this disclosure, a person of ordinary skill in the art would further recognize that the relative proportions of the components illustrated above could be varied without departing from the spirit and scope of the invention. It is understood, therefore, that this invention is not limited to that particular embodiment disclosed, but it is intended to cover modifications within the spirit and scope of the present invention as defined by the appended claims.

We claim:

1. A silicon-based cannabidiol derivative comprising at least one silicon-based functional group containing Si—O—Si bonds which is bound to a cannabidiol molecule having formula (I):

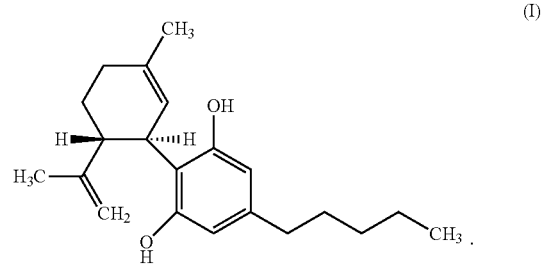 [SMILES: C=C(C)[C@@H]1CCC(C)=C[C@H]1c1c(O)cc(CCCCC)cc1O]

2. The silicon-based cannabidiol derivative according to claim 1, wherein the at least one silicon-based functional group is bound to the cannabidiol molecule by a phenolic oxygen atom in the benzenediol ring.

3. The silicon-based cannabidiol derivative according to claim 1, wherein the derivative comprises one silicon-based functional group bound to the cannabidiol molecule by the isopropenyl group.

4. The silicon-based cannabidiol derivative according to claim 1, wherein the derivative comprises one silicon-based functional group bound to the cannabidiol molecule by the isopropenyl group and at least one silicon-based functional group bound to the cannabidiol molecule by a phenolic oxygen atom in the benzenediol ring.

5. The silicon-based cannabidiol derivative according to claim 1, wherein the at least one silicon-based functional group is a siloxanyl group or trialkoxysilane-containing group.

6. The silicon-based cannabidiol derivative according to claim 1, wherein the at least one silicon-based functional group contains at least two silicon atoms.

7. The silicon-based cannabidiol derivative according to claim 1, having formula (A), (B), (C), (D), (E), or (F), wherein $R^1$, $R^2$, and $R^3$ are independently $SiMe(OSiMe_3)_2$ or $SiMe_2(OSiMe_2)_4CH_2CH_2CH_2CH_3$ (A)
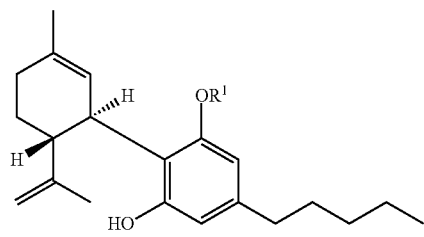

(B)
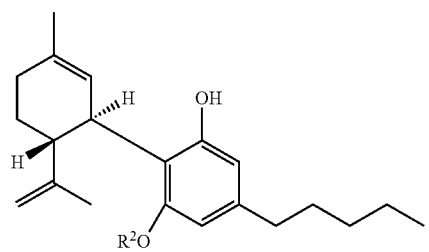

(C)
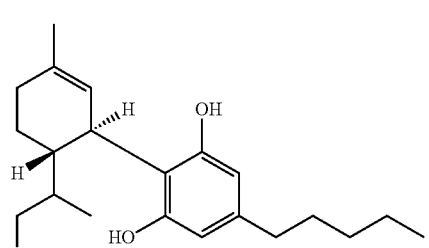

(D)
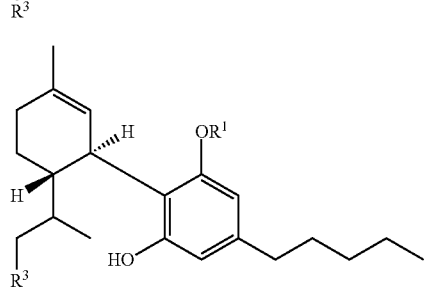

(E)
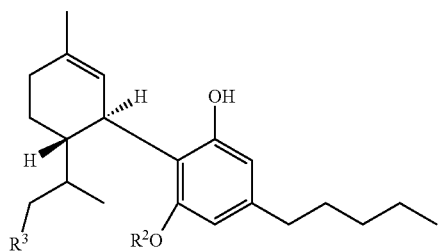

(F)
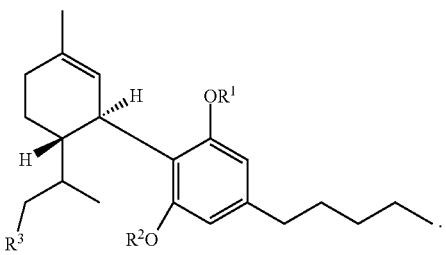

8. The silicon-based cannabidiol derivative according to claim 1, having formula (II):

(II)
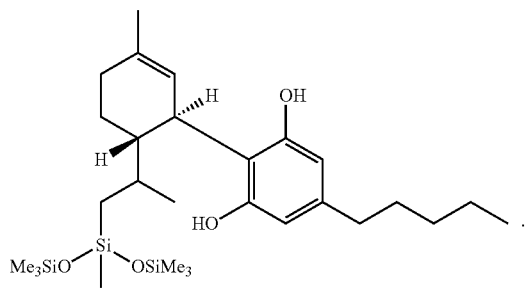

9. The silicon-based cannabidiol derivative according to claim 1, having formula (III):

(III)
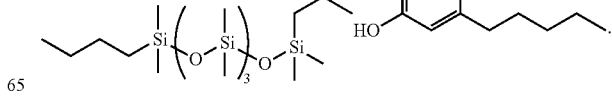

10. The silicon-based cannabidiol derivative according to claim 1, having formula (IV):

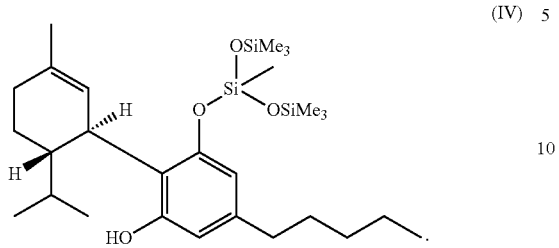
(IV)

11. The silicon-based cannabidiol derivative according to claim 1, having formula (V):

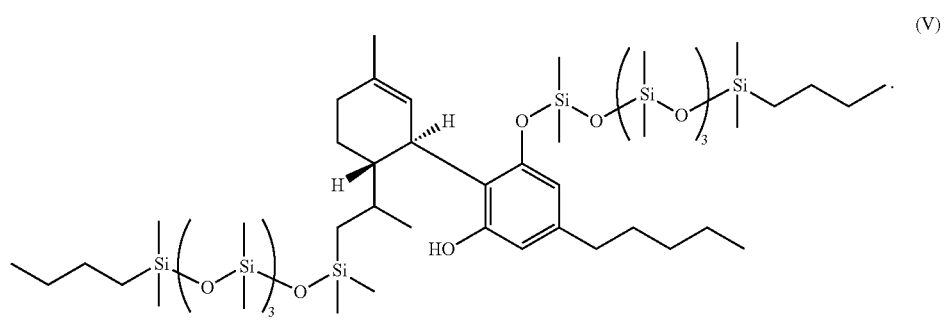
(V)

12. A cosmetic or topical composition comprising a base formulation and at least one silicon-based cannabidiol derivative, wherein the at least one silicon-based cannabidiol derivative comprises at least one silicon-based functional group containing Si—O—Si bonds which is bound to a cannabidiol molecule having formula (I):

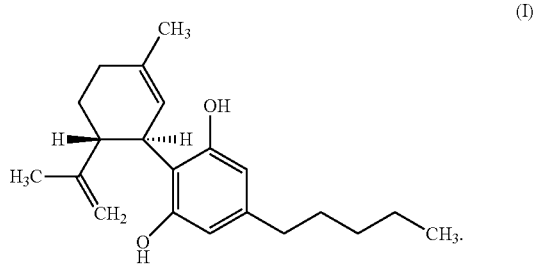 [SMILES: C=C(C)[C@@H]1CCC(C)=C[C@H]1c1c(O)cc(CCCCC)cc1O]
(I)

13. The cosmetic or topical composition according to claim 12, wherein the at least one silicon-based functional group is bound to the cannabidiol molecule by a phenolic oxygen atom in the benzenediol ring.

14. The cosmetic or topical composition according to claim 12, wherein the derivative comprises one silicon-based functional group bound to the cannabidiol molecule by the isopropenyl group.

15. The cosmetic or topical composition according to claim 12, wherein the derivative comprises one silicon-based functional group bound to the cannabidiol molecule by the isopropenyl group and at least one silicon-based functional group bound to the cannabidiol molecule by a phenolic oxygen atom in the benzenediol ring.

16. The cosmetic or topical composition according to claim 12, wherein the at least one silicon-based functional group is a siloxanyl group or trialkoxysilane-containing group.

17. The cosmetic or topical composition according to claim 12, wherein the at least one silicon-based functional group contains at least two silicon atoms.

18. A method for making the silicon-based cannabidiol derivative according to claim 1, comprising hydrosilylating the isopropenyl group of cannabidiol to form the silicon-based cannabidiol derivative.

19. A method for making the silicon-based cannabidiol derivative according to claim 1, comprising reacting cannabidiol with an allylic halide in a solvent to form an allyloxycannabidiol intermediate, and reacting the allyloxycannabidiol intermediate with a silane compound and a catalyst to form the silicon-based cannabidiol derivative.

20. A method for making the silicon-based cannabidiol derivative according to claim 1, comprising forming a silylated alkyl ether on a cannabidiol molecule by reacting a chlorine-containing siloxane compound with a hydroxyl group in the presence of a base acceptor.

21. A method for making the silicon-based cannabidiol derivative according to claim 1, comprising forming a silylated alkyl ether on a cannabidiol molecule by dehydrogenative coupling of a hydride-containing siloxane.

22. A method for making the silicon-based cannabidiol derivative according to claim 1, comprising forming a silylated alkyl ether on a cannabidiol molecule by forming an intermediate alkali metal alkoxide followed by reaction with a silicon-hydride or silicon-chlorine containing compound.

23. A composition comprising the silicon-based cannabidiol derivative according to claim 1 and at least one phytochemical extracted from hemp oil.

24. A composition comprising the silicon-based cannabidiol derivative according to claim 1 and a siloxane, wherein the composition spreads to a thin film which forms cannabidiol upon reaction with moisture.

25. A silicone elastomer or fluid infused with the composition according to claim 24.

* * * * *

UNITED STATES PATENT AND TRADEMARK OFFICE
CERTIFICATE OF CORRECTION

PATENT NO. : 10,933,008 B1
APPLICATION NO. : 16/879999
DATED : March 2, 2021
INVENTOR(S) : Barry C. Arkles et al.

Page 1 of 1

It is certified that error appears in the above-identified patent and that said Letters Patent is hereby corrected as shown below:

On the Title Page

Item (60) Related U.S. Application Data should read: Provisional application No. 62/925,945, filed on Oct. 25, 2019.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*